US00PP15056P3

(12) United States Plant Patent

Pecota et al.

(10) Patent No.: US PP15,056 P2

(45) Date of Patent: Aug. 3, 2004

(54) ORNAMENTAL SWEETPOTATO PLANT NAMED 'SWEET CAROLINE GREEN'

(50) Latin Name: *Ipomoea batatas*
Varietal Denomination: Sweet Caroline Green

(75) Inventors: Kenneth Pecota, Raleigh, NC (US); G. Craig Yencho, Washington, NC (US); Cynthia Pierce, Clayton, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 10/114,367

(22) Filed: Apr. 2, 2002

(65) Prior Publication Data

US 2003/0188358 P1 Oct. 2, 2003

(51) Int. Cl.[7] ..... A01H 5/00

(52) U.S. Cl. ..... Plt./258

(58) Field of Search ..... Plt./258

(56) References Cited

PUBLICATIONS

Armitage, Allan M. and James M. Garner, "*Ipomoea batatas* 'Margarita,'" *HortScience*: 36(1) 178 (Feb. 2001).
Armitage, Allan M., "Sweet Potato," *Greenhouse Grower*: 103–104 (Mar. 1999).
Baggett, "Sweet potato vines are morning glory cousins," *Fine Gardening*: 84 (Apr. 2002).
Bodger Seeds, Ltd., "2001 Pack Trials" invitation, Apr. 3–12, 2001.
Bodger Seeds, Ltd., "2001 Pack Trials" brochure, p. 13, Apr. 3–12, 2001.
Bodger Botanicals catalog, Sep./Oct.: p. 6 (2001).
North Carolina State University, "New Sweet Potatoes Add Ornamental Flavor," *Extension's Successful Garden*: p. 1 (Mar. 2002).
Online catalog selling Ipomea cultivars: www.glasshouse-works.com/trop–ij.html p. 4, date of access: Aug. 15, 2002.
Online catalog selling Ipomea cultivars: www.sunny-field.com/varietylists/companionplants.html p. 5, date of access: Aug. 15, 2002.
Online catalog selling Ipomea cultivars: www.pap-genos.com/plantdb/plants.asp?catid=15 p. 1–4, date of access: Aug. 15, 2002.
"Ornamental Sweet Potatoes," www.Inla.org/ornpotato.html pp. 1–2, updated Jun. 4, 2000, date of access: Aug. 15, 2002.
"Bodger Seeds/Botanicals," *Greenhouse Grower* (Jun. 2001).

*Primary Examiner*—Kent Bell
(74) *Attorney, Agent, or Firm*—Myers Bigel Sibley & Sajovec, P.A.

(57) ABSTRACT

A new and distinct ornamental cultivar of *Ipomoea batatas* called 'Sweet Caroline Green' is described that is a compact plant, with a round mounded shape, a dense canopy and dark green leaves that are deeply lobed. The plant is further distinguished by its unusual leaves, which have 3–5 narrow lobes, with prominent light green palmate veins. In addition, this cultivar has a reduced vigor as compared with existing cultivars of *Ipomoea batatas* known to the inventors. *Ipomoea batatas* 'Sweet Caroline Green' is suitable for use in landscaping and containerized gardens.

4 Drawing Sheets

Latin name of the genus and species: The Latin name of the novel, ornamental plant variety disclosed herein is *Ipomoea batatas* (L.) Lam.

Variety denomination: The inventive cultivar of *Ipomoea batatas* disclosed herein has been given the variety denomination 'Sweet Caroline Green'.

BACKGROUND OF THE INVENTION

Ipomoea species are members of the morning glory family Convolvulaceae. *Ipomoea batatas,* commonly referred to as the white or yellow sweetpotato and the orange yam, are typically fast growing vines with palmately-lobed leaves. These ornamental species produce storage roots identical in appearance to the common sweet potato, but not as palatable. Late in the growing season, tubular flowers appear which are similar to morning glories, but plantings are dominated by the appearance of the foliage. The plants are highly desirable due to their ability to grow under varied stress conditions, cover a large space, and last the entire growing season. Moreover, these plants have few insect or disease problems.

Existing varieties of *Ipomoea batatas* are popular for landscaping applications. There are currently six common types of ornamental sweetpotatoes that are being cultivated primarily for annual, summer vines. These six cultivars are: 'Blackie' (unpatented), having dark purple-black foliage, lavender flowers, and edible storage roots; 'Terrace Lime' (unpatented) and 'Margarita' (unpatented; also known as 'Sulfur'), which have large brilliant chartreuse leaves and lavender blooms; 'Black Heart' (unpatented; also known as 'Ace of Spades'), having heart-shaped leaves with burgundy purple color; 'Tricolor' (unpatented; also known as 'Pink Frost'), is a variegated plant which has pale green, white, and pink-margined leaves; and 'Lady Fingers', (unpatented), which has medium green, dainty leaves divided into long, thin, fingerlike lobes which are complemented by burgundy stems and veins.

*Ipomoea batatas* 'Margarita' has recently been released in the United States, and has become widely used as a landscape annual. It is not suitable for mixed containers, as it exhibits a very vigorous growth and tends to out-compete other species. Another popular variety is 'Blackie', a vigorous purple-leaved clone which is also unsuited to containerized gardens. See Armitage. A. M. and J. M. Garner. 2001. *Ipomoea batatas* 'Margarita'. *HortScience* 36:178.

Therefore, to meet the current horticultural demand, it is desirable to produce new, more robust cultivars of ornamental sweetpotato with attractive foliage colors, leaf shapes, and plant architectures. In addition, it would be advantageous to develop cultivars of ornamental sweetpotato exhibiting a more compact growth, and which do not out-compete other species in mixed containers.

The present invention comprises a new and distinct variety of *Ipomoea batatas,* which has been named 'Sweet Caroline Green'. The variety is suitable for use as a landscape or containerized plant.

Lineage. The *Ipomoea batatas* 'Sweet Caroline Green' cultivar originated from a conventional cross between *Ipomoea batatas* cultivars NC93-15XBL-1ORN (the female parent; not patented) and NCSXBR7-52ORN (the male parent; not patented) conducted in the Winter of 1998–1999 at the Horticultural Greenhouses located at North Carolina State University, Raleigh, N.C. NC93-15XBL-1ORN was a cross between an orange fleshed breeding line NC93-15 and 'Blackie'. NCSXBR7-52ORN was a cross between 'Sulfur' and 'Blackie'. Seeds from this cross were planted in the Horticultural Greenhouses in May 1999 and in a field at North Carolina State University in July 1999. The single, individual plant now known as *Ipomoea batatas* 'Sweet Caroline Green' was selected in October 1999 because of its combination of exceptional features, and has been propagated asexually since that time.

Asexual Reproduction. Since its selection, *Ipomoea batatas* 'Sweet Caroline Green' has been asexually reproduced at the Horticultural Greenhouses located at North Carolina State University, Raleigh, N.C. predominantly by vegetative propagation of vine cuttings. Asexual propagation of the new cultivar by cuttings at the location previously stated has shown that the unique features of this new Ornamental Sweetpotato are stable and the plant reproduces true to type in successive generations of asexual propagation.

SUMMARY OF THE INVENTION

The present *Ipomoea batatas* 'Sweet Caroline Green' ornamental plant is a compact rounded cultivar, having a dense canopy, with dark green leaves that are very deeply lobed. The unusual leaves have 3–5 narrow lobes with prominent light green palmate veins. Furthermore, this plant has a reduced vigor and growth rate as compared with other cultivars of *Ipomoea batatas* known to the inventors.

DETAILED BOTANICAL DESCRIPTION

The following is a detailed description of the botanical characteristics of a new and distinct cultivar of *Ipomoea batatas* plant known by the cultivar name *Ipomoea batatas* 'Sweet Caroline Green'. All colors cited herein refer to The Royal Horticultural Society Colour Chart (The Royal Horticultural Society, London, 1995 edition) designations except where general terms of ordinary dictionary significance are used. Where dimensions, sizes, colors, and other characteristics are given, it is to be understood that such characteristics are approximations or averages set forth as accurately as practicable.

The descriptions reported herein are from 12-week-old specimens grown individually in six-inch azalea pots. The plants were grown in Lompoc, Calif., under commercial practice in a polycarbonate-covered greenhouse during the 2001–2002 winter season with day and night temperatures ranging between 18.3–26.7° C. and 15.6–18.3° C., respectively, and light levels of about 4,000–8,000 foot-candles. *Ipomoea batatas* 'Sweet Caroline Green' has not been observed under all possible environmental conditions; therefore, the phenotype may vary with variations in the environment such as season, temperature, light intensity, day length, cultural conditions, and the like.

Growth Conditions. *Ipomoea batatas* 'Sweet Caroline Green' has good vigor, a moderate growth rate, and is very adaptable to container culture. In locales with mild winter conditions, *Ipomoea batatas* 'Sweet Caroline Green' will grow perennially; otherwise it is an annual plant that is killed by frost. In the greenhouse setting described above, after twelve weeks of growth, plants of this cultivar produce compact, round-mounded, herbaceous plants averaging 15 cm in height and 28 cm in length. Similar to cultivated sweetpotatoes, wind or rain rarely causes much damage to 'Sweet Caroline Green', but if damage does occur, the plant drops the damaged leaves and grows new shoots at nodes where the leaves were lost. Under low light levels in a greenhouse, 'Sweet Caroline Green' can develop intumescence, which will remain on the affected foliage, but will be outgrown with new foliage.

Figure 1:
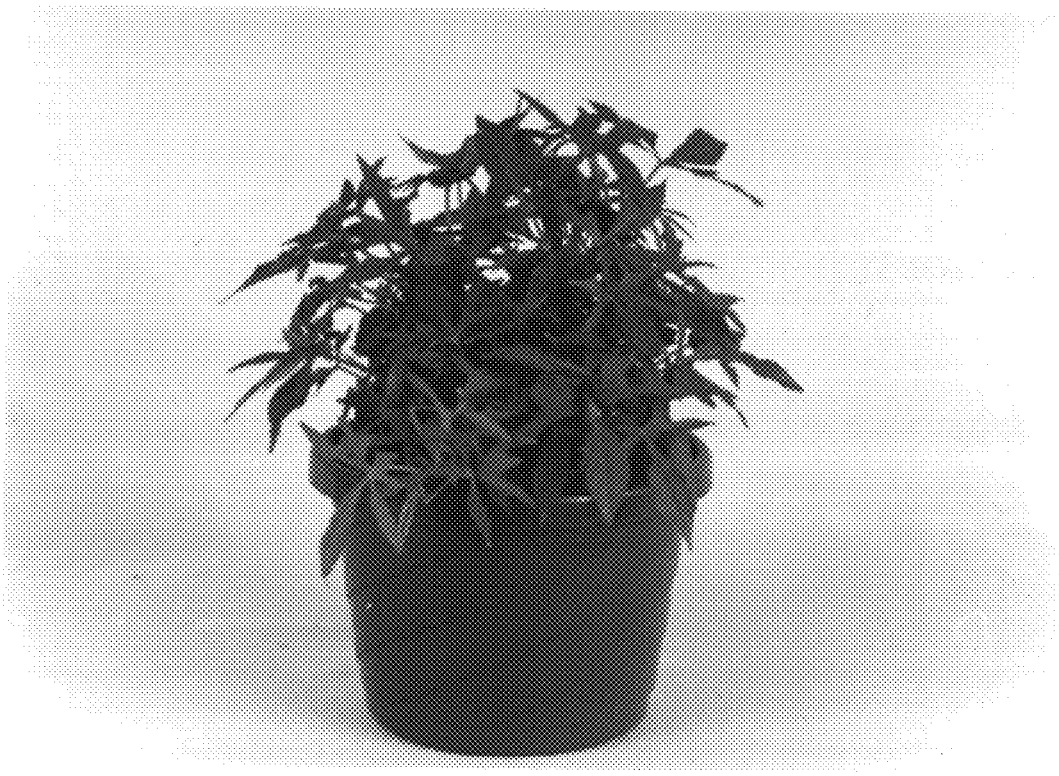
FIG. 1 is a color photograph of a typical plant of the *Ipomoea batatas* 'Sweet Caroline Green' grown in a container under commercial greenhouse conditions.
Figure 3:
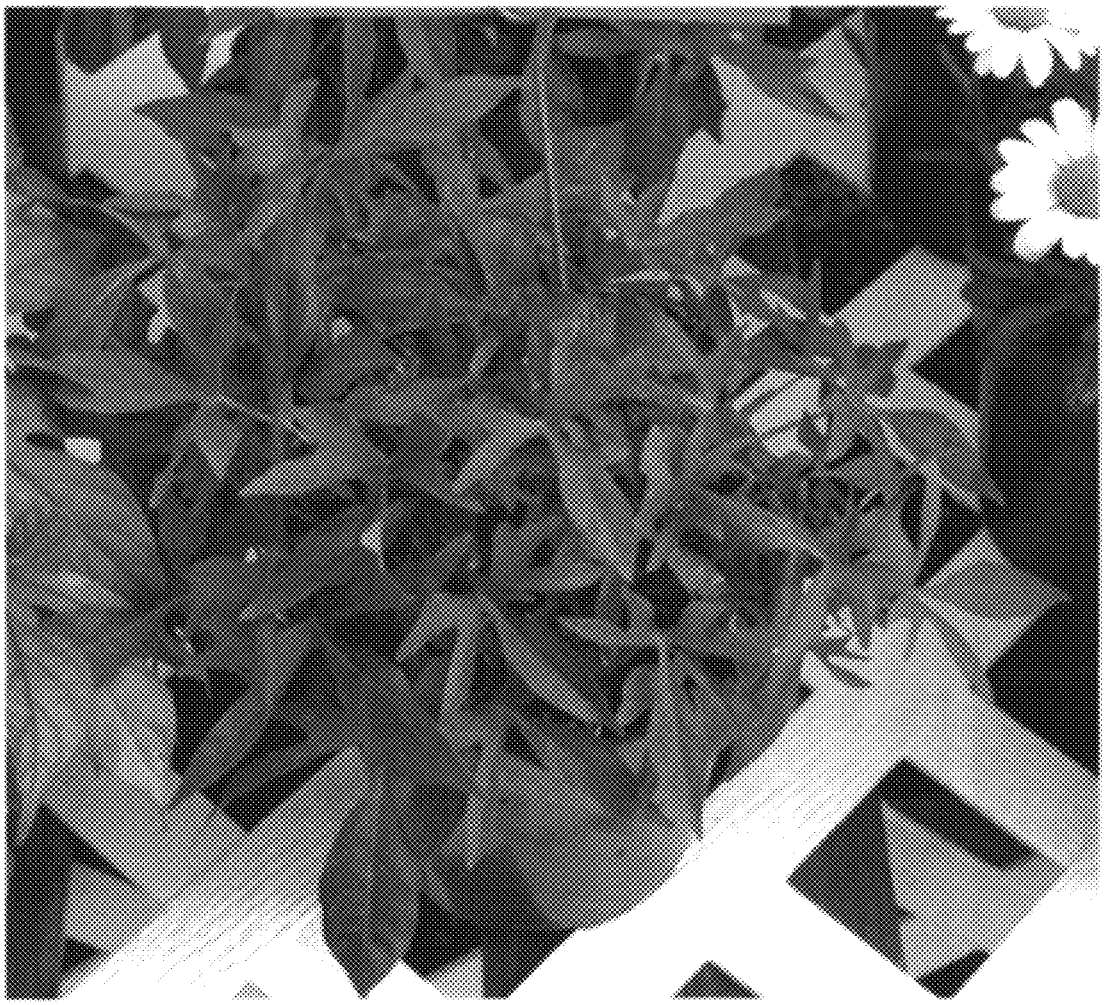
FIG. 3 shows a top view of a typical plant of the *Ipomoea batatas* 'Sweet Caroline Green' grown in a container under commercial greenhouse conditions.

Above-Ground Structure and Coloration. FIGS. 1 and 3 show the shape and coloration of typical plants of *Ipomoea batatas* 'Sweet Caroline Green'. Overall, this cultivar is a compact, mound shaped, and outwardly-spreading, herbaceous plant with a dense canopy and an average height of 15 cm and an average area of spread of 22×28 cm.

Branching Habitat. Freely-branching with approximately two basal branches and ~12 lateral branches per basal branch. Dense growth with no pinching required to stimulate branching.

Stem (Color: 144A). Round and smooth with an outward aspect and very good strength. Stem tends to undulate or zigzag between the alternate nodes. Length: ~10.0 cm, Diameter: ~0.4 cm. Internodes are stacked with an average length of ~0.8–1.0 cm.

Vegetative Lateral Branches (Color 144A). Same as stems for most characteristics. Length: ~10.0 cm. Diameter: ~0.4 cm. Internodes are stacked with an average length of ~0.8–1.0 cm.

Figure 2:
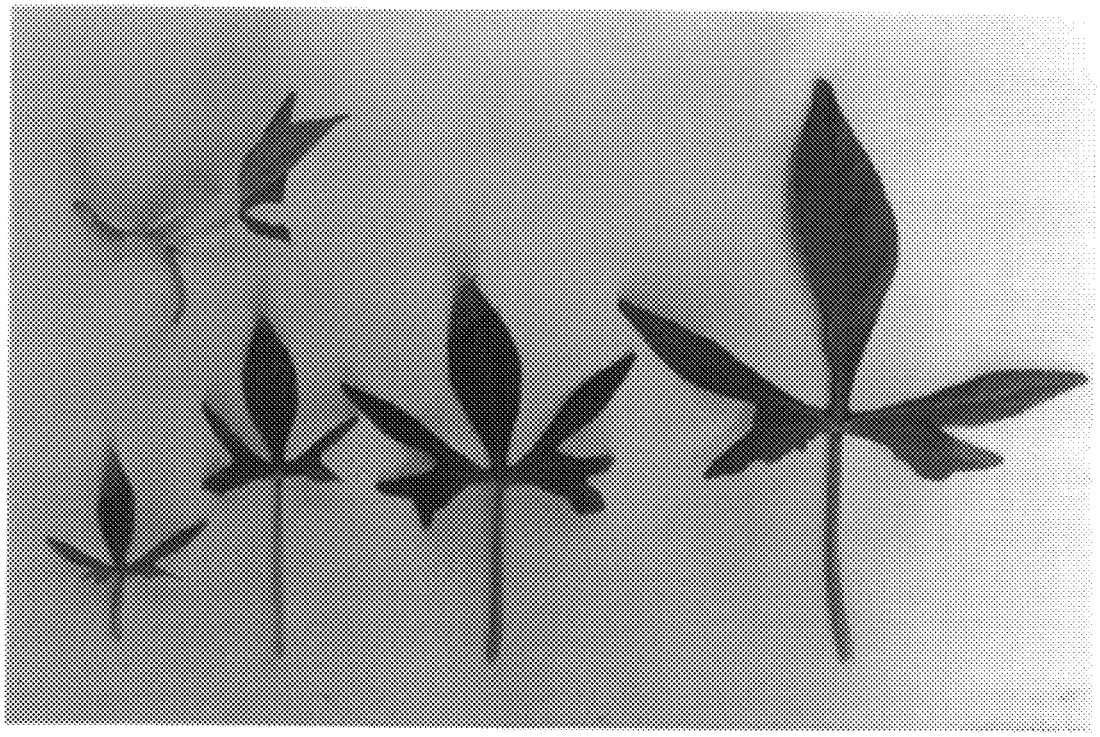
FIG. 2 shows the variety of leaves produced by *Ipomoea batatas* 'Sweet Caroline Green' and the lower surface of the leaf (upper left leaf).

Petiole (Color: 144B). Mature Petiole Length: ~6.5 cm with broad variation (see FIG. 2). Diameter: ~0.2 cm.

Foliage. Leaves are alternate and simple. Further, the leaves are palmate and are deeply divided into 3–5 lobes with sinuses nearly to the mid-vein. Quantity: Densely foliated, with ~10–12 leaves per lateral branch. Leaf shape is very consistent, but varies in size (see FIG. 2). Mature leaf length: ~6.0 cm. Mature leaf width: ~7.0 cm. Leaf margin is entire, but deeply divided. Lobe length: ~4.0 cm. Lobe width: ~0.8 cm. Mid-vein lobe width: ~1.7 cm. Leaf apex: Acute. Leaf base: Acute. Leaf has a smooth texture and matte finish. Venation is palmate at base with arcuate veins in the center lamina. Color: see Table 1.

TABLE 1

| Leaf Structure | Upper Surface | Lower Surface |
|---|---|---|
| Young Leaf | 138A | 147B |
| Mature Leaf | 147A | 147B |
| Vein | 147B | 147C |

Flowers. Cultivar 'Sweet Caroline Green' does flower sporadically throughout the season in response to a variety of stressful conditions (e.g., drought, nutrient stress, cloudy weather). Flowering is enhanced by shorter day lengths; however the precise photoperiod for flower induction is not known. The inflorescence is generally a cyme in which the peduncle is divided into two axillary peduncles. Each peduncle is further divided into two after the flower is produced. Usually buds of the first, second and third order are developed, but sometimes single flowers are produced. The corolla is composed of five fused petals that form a funnel with a round limb. Corolla width: ~3.5 cm, corolla length: ~3.6 cm. The corolla is not fragrant. The limb and outer throat are lavender and the inner throat purple. Inner limb color: 78D, Outer limb color: 78D, Inner throat color: 78A, Outer throat color: 78D. There are five sepals, which are elliptic with an acute apex and green in color. Each flower has one pistil, with a cream colored style. The stigma is cream colored and has two segments. The stigma is exerted relative to the stamens. The ovary is yellow and superior with two locules that contain one or two ovules. At the base of the ovary there are basal glands containing nectar. There are five cream colored anthers. Pollen is scarce. True seed are not easy to obtain because the plant does not flower readily and the seed set averages less than 15% true seed. There is some variation in flower size and color, depending on the environmental conditions. Descriptions are based on: CIP, AVRDC, IBPGR. 1991. Descriptors for Sweet Potato. Huaman, Z., editor. International Board for Plant Genetic Resources, Rome, Italy.

Figure 4:
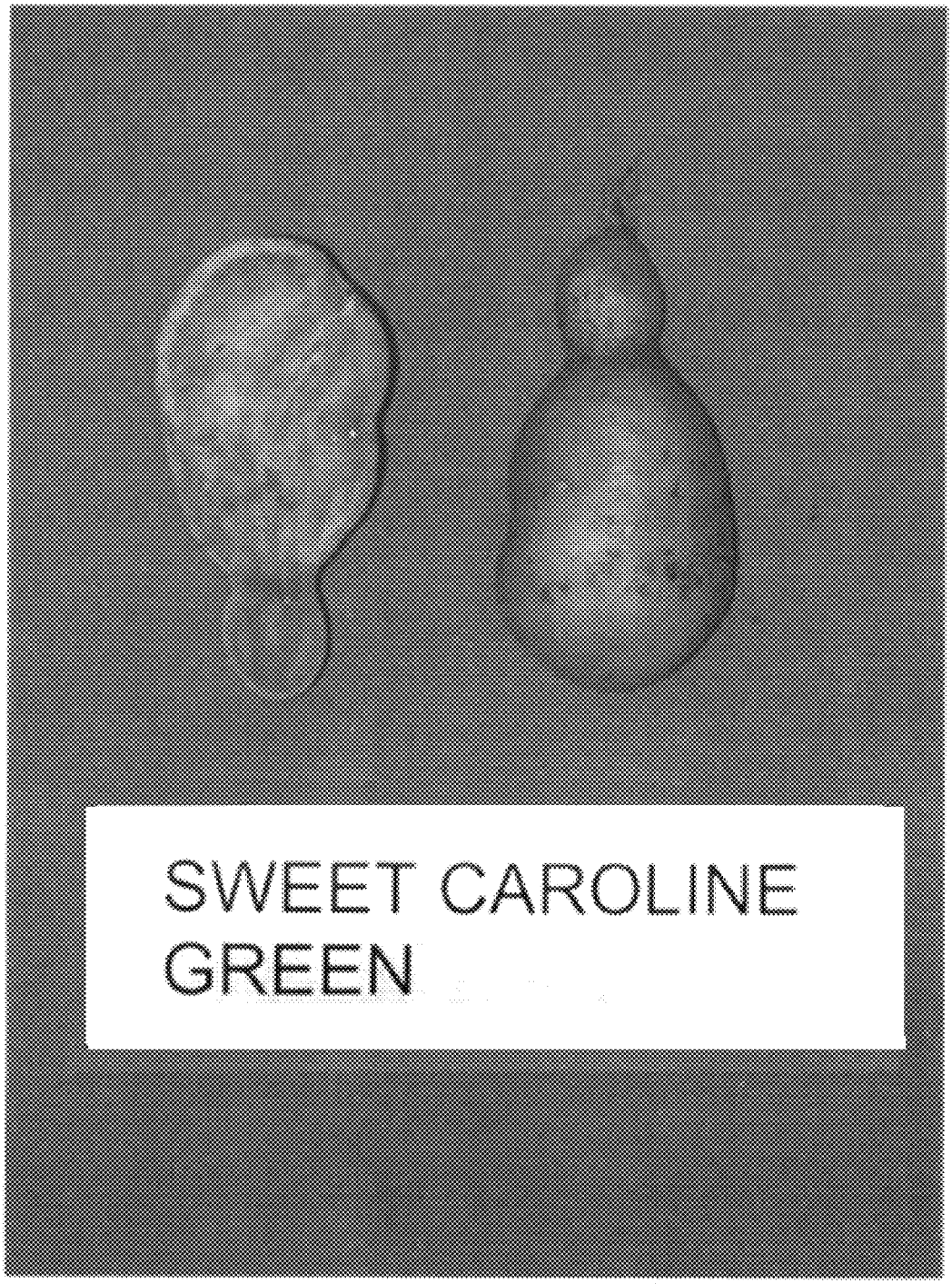
FIG. 4 shows the flesh and skin of a storage root.

Storage Roots. As shown in FIG. 4, the storage roots have a light orange skin (Color 165C) with predominantly light orange flesh (Color 159A) mottled with orange (Color 170C) and purple (Color 70B) flecks and a narrow (~2 mm) orange (Color 159A) ring notable under the epidermis. Shapes are highly irregular and vary considerably in length and diameter depending on growing conditions. A minimum of 150 days are needed to produce storage roots that meet the size criteria for United States Department of Agriculture (USDA) U.S. No. 1 grade (5.1–8.9 cm in diameter and 7.6 to 22.9 cm in length), but very few of these storage roots would meet the shape criteria for U.S. No. 1 grade. Under conditions in which the plant grows perennially, the storage roots will continue to grow as long as the roots are healthy and the weather remains warm.

Comparison With Other *Ipomoea batatas* Cultivars. Of the six most common cultivars of ornamental sweetpotato, *Ipomoea batatas* 'Sweet Caroline Green' most resembles the 'Lady Fingers' cultivar. Both cultivars are green and have deeply lobed leaves, but *Ipomoea batatas* 'Sweet Caroline Green' has green veins on the lower surface (see FIG. 2) and 'Lady Fingers' has purplish-red veins on the lower surface. Moreover, 'Lady Fingers' is the most vigorous of the ornamental *Ipomoea batatas* cultivars on the market, whereas 'Sweet Caroline Green' has a reduced vigor which makes it suitable for cultivation in a mixed container with other species. Furthermore, 'Sweet Caroline Green' has a compact, dense mound of foliage reaching a plant height of ~15 cm and 'Lady Fingers' has a trailing plant habit reaching a plant height of ~20 cm.

'Sweet Caroline Green' is quite distinct in its features as compared with its female parent, as shown in Table 2.

TABLE 2

| Leaf Structure | 'Sweet Caroline Green' | Female Parent NC93-15XBL-1ORN |
|---|---|---|
| Plant Habit | Compact | Trailing |
| Foliage Color | Green | Purple |
| Leaf Shape | Very Deeply Lobed Leaves | Very Deeply Lobed Leaves |

The male parent was used for crossing and has since been discarded. This variety had purplish-green foliage, but no other data were collected from this clone.

Disease or Pest Resistance. 'Sweet Caroline Green' is susceptible to Sweetpotato Feathery Mottle Virus and damage by Japanese beetles.

Herbarium voucher. A voucher of 'Sweet Caroline Green' will be deposited into the Herbarium of North Carolina State University (NCSU) in Raleigh, N.C. upon patenting.

What is claimed is:

1. A new and distinct cultivar of *Ipomoea batatas* plant named 'Sweet Caroline Green', substantially as illustrated and described herein.

* * * * *